US009125857B2

(12) United States Patent
Heger et al.

(10) Patent No.: US 9,125,857 B2
(45) Date of Patent: Sep. 8, 2015

(54) METHOD FOR PRODUCING A DRUG EXTRACT THAT CONTAINS HYDROXYSTILBENE

(76) Inventors: Peter Heger, Ubstadt-Weiher (DE); Reinhard Rettenberger, Göppingen (DE); Carl-Friedrich Spaich, Heiningen (DE)

(*) Notice: Subject to any disclaimer, the term of this patent is extended or adjusted under 35 U.S.C. 154(b) by 1452 days.

(21) Appl. No.: 11/883,687

(22) PCT Filed: Feb. 3, 2006

(86) PCT No.: PCT/EP2006/000955
§ 371 (c)(1),
(2), (4) Date: May 30, 2008

(87) PCT Pub. No.: WO2006/082071
PCT Pub. Date: Aug. 10, 2006

(65) Prior Publication Data
US 2009/0048184 A1   Feb. 19, 2009

(30) Foreign Application Priority Data

Feb. 4, 2005  (DE) ............ 10-2005-005-268
Feb. 4, 2005  (DE) ............ 10-2005-005-271

(51) Int. Cl.

| | |
|---|---|
| *A61K 31/70* | (2006.01) |
| *A61K 31/05* | (2006.01) |
| *A61P 5/24* | (2006.01) |
| *C07C 39/18* | (2006.01) |
| *C07G 3/00* | (2006.01) |
| *A61K 31/085* | (2006.01) |
| *A61K 31/7034* | (2006.01) |
| *A61K 36/15* | (2006.01) |
| *A61K 36/481* | (2006.01) |
| *A61K 36/482* | (2006.01) |
| *A61K 36/708* | (2006.01) |
| *A61K 9/28* | (2006.01) |
| *A61K 36/36* | (2006.01) |

(52) U.S. Cl.
CPC .......... *A61K 31/05* (2013.01); *A61K 9/2886* (2013.01); *A61K 31/085* (2013.01); *A61K 31/7034* (2013.01); *A61K 36/15* (2013.01); *A61K 36/36* (2013.01); *A61K 36/481* (2013.01); *A61K 36/482* (2013.01); *A61K 36/708* (2013.01)

(58) Field of Classification Search
USPC .............. 514/25, 733; 536/18.5; 568/729
See application file for complete search history.

(56) References Cited

U.S. PATENT DOCUMENTS

| | | |
|---|---|---|
| 2008/0026086 A1 | 1/2008 | Holyoak et al. |
| 2008/0248069 A1 | 10/2008 | Heger et al. |
| 2009/0042817 A1 | 2/2009 | Heger et al. |
| 2009/0137496 A1 | 5/2009 | Heger et al. |

FOREIGN PATENT DOCUMENTS

| | | | | |
|---|---|---|---|---|
| AU | A 26281 77 | * | 6/1977 | ............ C07G 17/00 |
| AU | 26281 77 A | | 1/1979 | |
| EP | 1 140 097 A | | 10/2001 | |
| EP | 1 161 944 A | | 12/2001 | |
| FR | 2 835 185 A | | 8/2003 | |
| FR | 2835185 A1 | * | 8/2003 | ............... A23L 1/30 |
| WO | WO 97/44407 A | | 11/1997 | |
| WO | WO 00/53176 | * | 9/2000 | ........... A61K 31/385 |
| WO | WO 01/08671 A1 | * | 2/2001 | ............ A61K 31/00 |
| WO | WO 03/039557 A | | 5/2003 | |
| WO | WO 03/039557 A1 | * | 5/2003 | ............ A61K 31/70 |
| WO | WO 2006/082068 A1 | | 8/2006 | |

OTHER PUBLICATIONS

Trisha Gura, Science, Nov. 1997, 1041-42.*
Loudon, M. Organic Chemistry, 1995, pp. 837-41.*
Gennaro, A.R., Remington: The Science and Practice of Pharmacy, 2000, p. 897.*
The Merck Manual, 16th Ed., 1992, pp. 339-342 and 1488-1490.*
Form PCT/IPEA/409, WO.
Matsuda, H. et al: "Phytoestrogens from the Roots of *Polygonum cuspidatum* (Polygonaceae): Structure-Requirement of Hydroxyanthraquinones for Estrogenic Activity". Bioorganic & Medicinal Chemistry Letters, 11 (2001) 1839-1842.
Babu, K.S., et al: "Yeast and Mammalian a-Glucosidase Inhibitory Constituents From Himalayan Rhubarb *Rheum emodi* Wall.ex Meisson". Bioorganic & Medicinal Chemistry Letters, 14 (2004) 3841-3845.
Alesci, S. et al., "Major Depression Is Associated with Significant Diurnal Elevations in Plasma Interleukin-6 Levels, a Shift of Its Circadian Rhythm, and Loss of Physiological Complexity in Its Secretion: Clinical Implications," J Clin Endocrinol Metab 2005; 90: 2522-2530.
Amorino, G.P., Parsons, S.J., "Neuroendocrine Cells in Prostate Cancer," Crit Rev Eukaryot Gene Expr 2004; 14: 287-300 (abstract).
Anisman, H. et al., "Cytokines as a Precipitant of Depressive Illness: Animal and Human Studies," Curr. Pharm. Des. 2005; 11: 963-972.
Ashikawa, K. et al., "Piceatannol Inhibits TNF-Induced NF-κB Activation and NF-κBα Kinase and p65 Phosphorylation," J. Immunol. 2002, 6490-6497.
Bachelot, T. et al., "Prognostic value of serum levels of interleukin 6 and of serum and plasma levels of vascular endothelial growth factor in hormone-refractory metastatic breast cancer patients," Brit. J. Cancer 2003; 88: 1721-1726.
WO-Form PCT/IPEA/409—English translation of International Preliminary Report on Patentability issued in PCT/EP06/000951.

(Continued)

*Primary Examiner* — Ganapathy Krishnan
(74) *Attorney, Agent, or Firm* — Saul Ewing LLP; Peter C. Lauro, Esq.

(57) ABSTRACT

The invention relates to a method for producing drug extracts that contain hydroxystilbene from a vegetable drug and to the use of various agents for pharmaceutical and non-pharmaceutical purposes.

27 Claims, No Drawings

(56) References Cited

OTHER PUBLICATIONS

Baker, A.E. et al., "Estrogen Modulates Microglial Inflammatory Mediator Production via Interactions with Estrogen Receptor β," Endrocrinol. 2004; 145: 5021-5032.

Bardin, A. et al., "Loss of ERβ espression as a common step in estrogen-dependent tumor progression," Endocrine-Rel. Cancer 2004; 11: 537-551.

Beduschi, M.C. et al., "Alpha-Blockade Therapy for Benign Prostatic Hyperplasia: From A Nonselective to a More Selective Alpha$_{1A}$—Adrenergic Antagonist," Urology 1998; 51: 861-872.

Belcher, Scott M. and Zsarnovszky, Attila, "Estrogenic Actions in the Brain: Estrogen, Phytoestrogens, and Rapid Intracellular Signaling Mechanisms," J. Pharmacol. Exp. Therap. 2001; 299: 408-414.

Beral, V. et al., "Evidence from randomised trials on the long-term effects of hormone replacement therapy," Lancet 2002; 360: 942-944.

Chapple, C.R., "Pharmacological therapy of benign prostatic hyperplasia/lower urinary tract symptoms: an overview for the practising clinician," BJU Int. 2004; 94: 738-744.

Cheblowski, R.T. et al., "Influence of Estrogen Plus Progestin on Breast Cancer and Mammography in Healthy Postmenopausal Women," JAMA 2003; 289: 3243-3253.

Cheng, J. et al., "Expression of estrogen receptor β in prostate carcinma cells inhibits invasion and proliferation and triggers apoptosis," FEBS Lett. 2004; 566: 169-172.

Curran, E.M. et al., "Natural Killer Cells Express Estrogen Receptor-α and Estrogen Receptor-β and Can Respond to Estrogen Via a Non-Estrogen Receptor-α-Mediated Pathway," Cell. Immunol. 2001; 214: 12-20.

Dijsselbloem, N. et al., "Soy isoflavone phyto-pharmaceuticals in interleukin-6 affections Multi-purpose nutraceuticals at the crossroad of hormone replacement, anti-cancer and anti-inflammatory therapy," Biochem Pharmacol. 2004; 68: 1171-1185.

Dinarello, C.A., "Therapeutic strategies to reduce IL-1 activity in treating local and systemic inflammation," Curr. Op. Pharmacol. 2004; 4: 378-385.

Dizeyi, N. et al., "Expression of Serotonin Receptors and Role of Serotonin in Human Prostate Cancer Tissue and Cell Lines," Prostate 2004; 59: 328-336.

Donovan, J.L., "The measurement of symptoms, quality of life and sexual function," BJU Int. 2000, 85, Suppl. 1: 10-19 (abstract).

Drachenberg, Darrel E. et al., "Circulating Levels of Interleukin-6 in Patients With Hormone Refractory Prostate Cancer," Prostate 1999; 41: 127-133.

Dunn, C.J. et al., "Tamsulosin: a review of its pharmacology and therapeutic efficacy in the management of lower urinary tract symptoms," Drugs Aging 2002; 19: 135-161 (bstract).

Enmark, E. et al., "Human Estrogen Receptor β-Gene Structure, Chrmosomal Localization, and Expression Pattern," J. Clin. Endocrinol. Metab. 1997; 82: 4258-4265.

Frasor, J. et al., "Response-Specific and Ligand Dose-Dependent Modulation of Estrogen Receptor (ER) α Activity by ERβ in the Uterus," Endocrinol. 2003; 144: 3159-3166.

Galien, R. et al., "Estrogen receptor impairs interleukin-6 expression by preventing protein binding on the NK-κB site," Nucleic Acids Res. 1997; 25: 2434-2439.

Gao, S. et al., "Modulation of Androgen Receptor-Dependent Transcription by Resveratrol and Genistein in Prostate Cancer Cells," The Prostate 2004; 59: 214-225.

George, D.J. et al., "The Prognostic Significance of Plasma Interleukin-6 Levels in Patients with Metastatic Hormone-Refractory Prostate Cancer: Results from Cancer and Leukemia Group B 9480," Clin Cancer Res 2005, 11: 1815-1820.

Gilbert, C., "Major human cancers are preventable: physiological stimuli induce a dopamine-thyroid-immune efficient mechanism," E J. Cancer Prev 1997; 6: 269-276 (abstract).

Guerini, V. et al., "The Androgen Derivative 5α-Androstane-3β, 17β-Diol Inhibits Prostate Cancer Cell Migration Through Activation of the Estrogen Receptor β Subtype," Cancer Res 2005; 65: 5445-5453.

Hanstein, B. et al., "Insights into the molecular biology of the estrogen receptor define novel therapeutic targets for breast cancer," Eur. J. Endocrinol. 2004; 150: 243-255.

Harris, H.A. et al., "A selective estrogen receptor-β agonist causes lesion regression in an experimentally induced model of endometriosis," Hum. Reprod. 2005; 20: 936-941.

Harris, H.A. et al., "Evaluation of an Estrogen Receptor-β Agonist in Animal Models of Human Disease," Endocrinol. 2003; 144: 4241-4249.

Henderson, T.A. et al., "Steroid Receptor Expression in Uterine Natural Killer Cells," J. Clin. Endocrinol. Metab. 2003; 88: 440-449.

Imamov, O. et al., "Estrogen Receptor β in Prostate Cancer, " N. Engl. J. Med. 2004; 351: 2773-2774.

Imwalle, D.B. et al., "Lack of functional estrogen receptor β influences anxiety behavior and serotonin content in female mice," Physiology & Behavior 2005; 84: 157-163.

Jiang, X. P. et al., "Recuction in Serum IL-6 After Vacination of Breast Cancer aPatients with Tumour-Associated Antigens is Related to Estrogen Receptor Status," Cytokine 2000; 12: 458-465.

Konig, J.E. et al., "Analysis of the Inflammatory Network in Benign Prostate Hyperplasia and Prostate Cancer," Prostate, 2004; 58: 121-129.

Krege, J. H. et al., "Generation and reproductive phenotypes of mice lacking estrogen receptor β," Proc. Natl. Acad. Sci USA, 1998; 95: 15677-15682.

Kuiper, G. G. J. M. et al., "Comparison of the Ligand Binding Specificity and Transcript Tissue Distribution of Estrogen Receptors α and β," Endocrinol. 1997, 138: 863-870.

Kuiper, G. G. J. M. et al., "Cloning of a novel estrogen receptor expressed in rat prostate and ovary," Proc. Natl. Acad. Sci, USA, 1996; 93: 5925-5930.

Lepor, H., "Phase III Multicenter Placebo-Controlled Study of Tamsulosin in Benign Prostatic Hyperplasia," Urology 1998; 51 (6): 892-900.

Long, R and Gardam, M., "Tumour necrosis factor-α inhibitors and the reactivation of latent tuberculosis infection," CMAJ 2003; 168: 1153-1156.

Lund, T.D. et al., "Novel Actions of Estrogen Receptor-β on Anxiety-Related Behaviors," Endocrinology 2005; 146: 797-807.

Matsuda, H. et al., "Study on Anti-Oketsu Activity on Rhubarb II. Anti-allergic Effects of Stilbene Components from Rhei undulati Rhizoma (Dried Rhizome of *Rheum undulatum* Cultivated in Korea)," Biol. Pharm. Bull. 2001, 24(3)): 264-267.

Million women Study Collaborators: "Breast cander and hormone-replacement therapy in the Million Women Study," Lancet 2003; 362: 419-427.

Morris, G. Z. et al., "Resveratrol Induces Apoptosis in LNCaP Cells and Requires Hydroxyl Groups to Decrease Viability in LNCaP and DU 145 Cells," The prostate 2002, 52, 319-329.

Motivala, S. J. et al., "Inflammatory Markers and Sleep Disturbance in Major Depression," Psychosom Med 2005; 67: 187-194.

Park, Woo-Chan and Jordan, V. Craig, "Selective estrogen receptor modulators (SERMS) and their roles in breast cancer prevention," Trends Mol. Medicine 2002; 8: 82-88.

Park, Eun-Kyung et al., "Antithrombotic and Antiallergic Activities of Phaponticin from Rhei Rhizoma Are Activated by Human Intestinal Bacteria," Arch. Pharm. Res. 2002, 25(4), 528-533.

Peters, D. J. and Sorkin, E. M., "Finasteride," Drugs 1993; 46: 177-208.

Pfeilschifter, J. et al., "Changes in Proinflammatory Cytokine Activity after Menopause," Endocrine Rev. 2002; 23: 90-119.

Reuter, U. et al., "Nuclear Factor-κB as a Molecular Target for Migraine Therapy," Ann Neurol 2002; 51: 507-516.

Roberti, M. et al., "Synthesis and Biological Evaluation of Resveratrol and Analogues as Apoptosis-Inducing Agents," J. Med. Chem. 2003, 46, 3546-3554.

Rocha, B.A. et al., "17beta-Estradiol-induced antidepressant-like effect in the Forced Swim Test is absent in estrogen receptor-beta knockout (BERKO) mice," Psychopharmacology 2005, 179: 637-643 (abstract).

Siddiqui, E.J. et al., "The role of serotonin in tumour growth (review)," Oncol Rep 2005; 14: 1593-1597 (abstract).

(56) References Cited

OTHER PUBLICATIONS

Spinelli, M.G., "Depression and Hormone Therapy," Clin Obstet Gynecol 2004; 47: 428-436.
Stein, B. and Yang, M.X., "Repression of the Interleukin-6 Promoter by Estrogen Receptor Is Mediated by NF-κB and C/EBPβ," Mol Cell Biol. 1995; 15: 4971-4979.
Stygar, D. et al., "Co-localization of oestrogen receptor β and leukocyte markers in the human cervix," Mol. Hum. Reprod. 2001; 7: 881-886.
Trikha, M. et al., "Targeted Anti-Interleukin-6 momoclonal Antibody Therapy for Cancer: A Review of the Rationale and Clinical Evidence," Clin Cancer Res. 2003; 9: 4653-4665.
Unfer, V. et al., "Endometrial effects of long-term treatment with phytoestrogens: a randomized, double-blind, placebo-controlled study," Fertil Seril 2004; 82: 145-148.
Vegeto, E. et al., "Estrogen Prevents the Lipopolysaccharide-Induced Inflammatory Response in Microglia," J. Neurosci. 2001; 21: 1809-1818.
Walf, A.A. and Frye, C.A., "ERβ-Selective Estrogen Receptor Modulators Produce Antianxiety Behavior when Administered Systemically to Ovariectomized Rats," Neuropsychopharmacology 2005; 30: 1598-1609.
Weihua, Z. et al., An endocrine pathway in the prostate, ERβ, AR, 5α-androstane-3β, 17ζ-diol, and CYP7B!, regulates prostate growth,: Proc. Natl. Acad. Sci USA, 2002; 99: 13589-13594.
Wen, Y. et al., "Estrogen attenuates nuclear factor-kappa B activation induced by transient cerebral ischemia," Brain Res. 2004; 1008: 147-154.
Writing Group for the Women's Health Initiative Investigators, "Risks and Benefits of Estrogen Plus Progestin in Healthy Postmenopausal Women," JAMA 2002; 288: 321-333.
Miller & O'Callaghan, Metab Clin Exp 2005; 54: 33-38.
Kageura T et al: "Inhibitors from rhubarb on lipopolysaccaride-induced nitric oxide production in macrophages: Structural requiements of stilbenes for the activity" Bioorganic and Medicinal Chemistry 2001 United Kingdom, vol. 9 No. 7, 2001, pp. 1887-1893, XP002378711, ISSN: 0968-0896.
Ko S K et al: "Effects of stilbene derivatives from *Rheum undulatum* on carrageenan-induced acute edema in rats" Korean Journal of Pharmacognosy 2004 South Korea, vol. 35, No. 2, 2004, pp. 171-174, XP009065748, ISSN: 0253-3073.
Ryu S Y et al: "Antititumor activity of some phenolic components in plants" Archives of Pharmacal Research Natl. Fisheries University, Pusan, KR. vol. 17, No. 1, Jan. 1994, pp. 42-44, XP002968965, ISSN: 0253-6269.
Chun Young Jin et al: "Mechanism-based inhibition of human cytochrome P450 1A1 by rhapontigenin" Drug Metabolism and Disposition, vol. 29, No. 4 Part 1, Apr. 2001, pp. 389-393, XP002378712, ISSN: 0090-9556.
Waffo-Teguo Pierre et al: "Potential cancer-chemopreventive activities of wine stilbenoids and flavans extracted from grape (*Vitis vinifera*) cell cultures" Nutrition and Cancer, vol. 40, No. 2, 2001, pp. 173-179, XP009065742, ISSN: 0163-5581.
Anonym: "Phytoestrogen hilft bei Beschwerden im Klimakterium" Arzte Zeitung, [Online], May 16, 2000, XP002378130, Retrieved from the Internet, the whole document.
Rote Liste Service GmbH (Ed.): "Rote Liste", 2002, Editio Cantor Verlag, Aulendorf, XP002379296, Eintrag 760001 "Phytoestrol N".
Aggarwal B B et al: "Role of resveratrol in prevention and therapy of cancer: Preclinical and clinical studies". Anticancer Research 2004 Greece, vol. 24, No. 5 A, 2004, pp. 2783-2840, XP009065753, ISSN: 0250-7005, the whole document.
Sabichi A L et al: "COX-2 inhibitors and other nonsteroidal anti-inflammatory drugs in genitourinary cancer" Seminars in Oncology 2004 United States, vol. 31, No. Suppl. 7, 2004, pp. 36-44, XP009066086, ISSN: 0093-7754, p. 38, col. 1, paragraph 3.
Matsuda et al., "Phytoestrogens from the Roots of *Polygonum cuspidatum* (Polygonaceae): Structure-Requirement of Hydroxyanthraquinones for Estrogenic Activity", Bioorganic & Medicinal Chemistry Letters 11 (2001) 1839-1842.
Masuda et al., "Microsomal transformation of emodin into a direct mutagen." (Abstract), Mutat Res. Feb. 1984; 125(2): 135.44.
Donnelly, et al., "Anti-inflammatory effects of resveratrol in lung epithelial cells: molecular mechanisms", AM J Physiol Lung Cell Mol Physiol 287 (2004); L 774-L783.
Sugiyama, et al., "ER beta.: recent understanding of estrogen signaling", Trends in Endo. and Metabolism, 21 (2010): 545-552.
Obi, et al., "The Use of Herbal Preparations to Alieviate Climacteric Disorders and Risk of Postmenopaulal Breat Cancer in German Case-Controlled Study", Cancer Epiderniol Biomarkers Prev. 2009, 18(8), 2207-2213.
Wober, et al., Journal of Steroid Biochemistry and Molecular Biology 107 (2007) 191-201.
Kaszkin-Bettag, et al., Alternative Therapies. Jan./Feb. 2009, vol. 15, No. 1.
Colditz, et al., New England Journal of Medicine 1995; 332: 1589-1593.
Hewitt, et al., Breast Cancer Research 2000; 2: 345-352.
Ross, et al., J. Natl. Cancer Inst. 2000; 92: 328-332.
Schairer, et al., JAMA 2000; 283: 485-491.
Unfer, et al., Fertil Steril 2004; 82:145-148.
Abstract for Aerztezeitung May 16, 2000. "Phytoestrogen hilft bei Beschwerden im Klirnakterium", (English Translation).
Y. Yazaki, W. E. Hills, Polyphenclic extractives of *Pinus radiata*, Holzforschung 1977, 31, 20-25.

* cited by examiner

METHOD FOR PRODUCING A DRUG EXTRACT THAT CONTAINS HYDROXYSTILBENE This application is the U.S. national phase application, pursuant to 35 U.S.C. §371, of PCT international application Ser. No. PCT/EP2006/000955, filed Feb. 3, 2006, designating the United States and published in German on Aug. 10, 2006 as publication WO 2006/082071 A1, which claims priority to German application Ser. Nos. DE 10 2005 005 268.1, filed Feb. 4, 2005 and DE 10 2005 005 271.1, filed Feb. 4, 2005. The entire contents of the aforementioned patent applications are incorporated herein by this reference.

The invention relates to a process for producing a hydroxystilbene-containing drug extract from a herbal drug and the use of the drug extracts produced in this way for producing various compositions for pharmaceutical and non-pharmaceutical purposes.

BACKGROUND OF THE INVENTION

The collective term hydroxystilbenes encompasses a large group of compounds which can be obtained as natural constituents of herbal drugs or by chemical synthesis and some of which have pharmacological activity.

Thus, for example, Aggarwal et al. describe in a review article (Anticancer Research, 24, 2004) resveratrol and structurally similar compounds and the natural sources thereof.

Because of the potential pharmacological use of naturally occurring hydroxystilbenes and hydroxystilbene mixtures, there is a need to develop processes making it possible to isolate desired hydroxystilbenes reliably and reproducibly on the industrial scale and moreover in adequate purity and yield.

FR 2 835 185 describes a complex rhubarb extract obtainable from rhizomes of *Rheum rhaponticum*, which is said to be characterized in that it comprises at least 50% hydroxystilbenes, with at least 50% of these hydroxystilbenes consisting of rhaponticin, deoxyrhaponticin, astrangin and piceatannol. A preferred extract comprises 15-50% by weight rhaponticin, 10-35% by weight deoxyrhaponticin, 5-10% by weight astrangin and 0.1-3% by weight piceatannol. This extract is, as illustrated in the examples, prepared by hydroalcoholic extraction of rhizomes of *Rheum rhaponticum*. The total content of rhaponticin and deoxyrhaponticin which can be obtained thereby is only 76% by weight. The content of astrangin comprises 11% by weight, the content of piceatannol comprises 3% by weight, and the content of anthracenosides comprises 0.5% by weight. In addition thereto, this extract appears to comprise about 10% by weight further undefined constituents. It is additionally asserted in FR 2 835 185 that the specific extract therein has, as a result of alleged synergistic effects of the various ingredients of the extract, biological properties which are considerably superior to the effect of the individual hydroxystilbenes, especially those effects which the ingredients described therein are said to have individually. The extract described therein is alleged to have antioxidant, antitumor, antiinflammatory and estrogenic properties. However, in fact, FR 2 835 185 does not provide a verifiable technical teaching for the asserted pharmacological usability, to say nothing of the asserted synergistic effect of the complex drug extract described therein. The experimental section describes merely individual formulation examples of capsules, tablets or creams. In particular, experimental data proving the alleged usability for the treatment of disorders connected with free radicals, such as, for example, accelerated aging, cancer, arteriosclerosis, wrinkles, inflammatory phenomena and the like, are completely lacking. The asserted suitability of a combination of the rhubarb extract described therein with a hop extract rich in prenyl flavonoids for the treatment of diseases standing with free radicals and/or for the treatment of hormonal imbalance such as amenorrhea, menopause, hot flushes etc., is not proved by any data either. It is moreover entirely unclear which of the components actually present in the extract described therein (rhaponticin, deoxyrhaponticin, astrangin, piceatannol, anthracenosides, and the unanalyzed constituents present in a content of 10%) contribute to the asserted pharmacological activity or, where appropriate, are in fact absolutely necessary for the asserted synergism. The actual disclosure of FR 2 835 185 should therefore be restricted to the preparation of a specific, complex rhubarb extract by hydroalcoholic extraction of rhizomes of *Rheum rhaponticum* and the preparation of specific hydroxystilbene derivatives, and the production of various pharmaceutical formulations.

Numerous further publications (cf., for example, Babu et al., Bioorg. Med. Chem. Lett. 14 (2004), 3841-3845; Matsuda et al., Bioorg. Med. Chem. 9 (2001), 41-50) propose the use of methanol as extractant for extracting the constituents of *Rheum rhizoma*.

EP-A-1 140 097 describes the isolation of trihydroxystilbene compounds from plant material by extraction with aqueous solvent, followed by a specific combination of chromatographic steps. The aqueous solvent is in particular an alcohol-water mixture comprising 75% alcohol. Pure water is not used as extractant. Typical extracted plants are *Vitis vinifera* and *Polygonum cuspidatum*.

However, the extracts obtained according to the prior art have very complex compositions, have only limited suitability as such for medical use, and require further purification steps.

There is thus a need for an improved process for producing hydroxystilbene-containing drug extracts.

SUMMARY OF THE INVENTION

The object of the present invention is to provide an efficient process for producing a hydroxystilbene-containing drug extract. An object of the invention is in particular to produce a drug extract which is particularly pure and includes as predominant hydroxystilbene constituents the glycone forms (glycosides) of hydroxystilbenes such as, in particular, rhaponticin and deoxyrhaponticin.

It has surprisingly been possible to achieve the above object by providing an extraction process which is described in detail in the following sections.

DETAILED DESCRIPTION OF THE INVENTION

1. Preferred Aspects of the Invention

The invention relates to a process for producing a hydroxystilbene-containing drug extract, where
a) a hydroxystilbene-containing part of a medicinal plant, where appropriate in a form comminuted in a conventional way, is provided,
b) an aqueous, organic or aqueous-organic extractant is added thereto,
c) after the extractant has acted, a liquid extract phase is obtained from the mixture, and the extraction is repeated several times where appropriate, and
d) the extractant is removed from the liquid extract phases obtained in this way.

A particular aspect is a process in which the hydroxystilbene-containing part of a medicinal plant comprises at least one piceatannol and/or resveratrol prodrug.

Hydroxystilbenes in the sense of the invention include in particular sugar-containing (glycosides) and sugar-free (aglycones) prodrugs (i.e. precursors or derivatives) of resveratrol and piceatannol. Resveratrol and piceatannol prodrugs in the sense of the invention are in particular also substances which can be converted into resveratrol and/or piceatannol in vivo, such as, for example, in humans and/or another mammal, such as, for example, dog. Typical glycosides in this connection are rhaponticin, deoxyrhaponticin and astringin; typical aglycone precursors are rhapontigenin and deoxyrhapontigenin, without being restricted thereto (cf. also Table 1 and following structural formula).

The terms "prodrug" or "precursor" are, however, not to be understood as functional restriction in the context of the invention. As can be proven by various experimental results, in particular the "precursors" of the invention per se likewise display advantageous pharmacological effects.

It is possible according to the invention for hydroxystilbenes to be present as salt or in phenolic form, in a stereoisomeric form such as cis or trans form, or as mixture of such stereoisomeric forms in the drug, or to be obtained as products of the process.

TABLE 1

| Hydroxystilbene | Chemical name | CAS No. |
|---|---|---|
| Rhaponticin | 3,3',5-Trihydroxy-4'-methoxystilbene-3-O-β-D-glucopyranoside | 155-58-8 |
| Deoxyrhaponticin | 3',5-Dihydroxy-4'-methoxystilbene-3-O-β-D-glucopyranoside | 30197-14-9 |
| Rhapontigenin (trans-Rhapontigenin) | 3,3',5-Trihydroxy-4'-methoxystilbene | 500-65-2 |
| Deoxyrhapontigenin | 3',5-Dihydroxy-4'-methoxystilbene | 33626-08-3 |

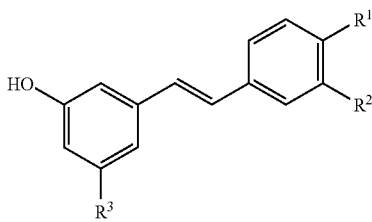

| | $R^1$ | $R^2$ | $R^3$ |
|---|---|---|---|
| Resveratrol | OH | H | OH |
| Rhaponticin | OCH$_3$ | OH | O-Glc |
| Deoxyrhaponticin | OCH$_3$ | H | O-Glc |
| Rhapontigenin | OCH$_3$ | OH | OH |
| Deoxyrhapontigenin | OCH$_3$ | H | OH |
| Astringin | OH | OH | O-Glc |
| Piceatannol (astringenin) | OH | OH | OH |

The invention relates in particular to a process where the resulting extract includes at least one compound selected from rhaponticin, deoxyrahponticin, rhapontigenin, deoxyrhapontigenin as salt or in phenolic form, in a stereoisomeric form, or as mixture of such stereoisomeric forms.

The extracted hydroxystilbenes are, however, preferably substantially present in the trans form. Salts are in particular the alkali metal and alkaline earth metal phenolates of the above compounds which have one or more free phenolic hydroxyl groups. If a plurality of hydroxyl groups is present, these can be partly or completely in the salt form.

The resulting plant extracts or individual components thereof can also be subjected to derivatization reactions in order to obtain so-called functional derivatives. These are in particular derivatives which can be converted back in the human or animal body, after administration, into the underivatized starting compound again. Mention should be made in particular of ethers and ester derivatives of the compounds used according to the invention. It is moreover possible for individual ones or all of the etherifiable or esterifiable groups in a molecule (especially the phenolic and glycosidic hydroxyl groups) to be derivatized. Examples of suitable derivatives and their preparation are described for example in FR 2 835 185, which is incorporated herein by reference. Thus, mention may be made of, without being restricted thereto: esters of saturated or unsaturated, aliphatic or aromatic carboxylic acids having up to 25 carbon atoms, such as 1 to 25 carbon atoms, such as, for example, saturated $C_6$-$C_{22}$ fatty acids (such as, for example, saturated unbranched fatty acids selected from caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid); or silyl ethers, where the silicon atom carries three identical or different, straight-chain or branched, saturated or unsaturated hydrocarbon radicals having up to 20 carbon atoms, such as, for example, $C_1$-$C_{20}$ alkyl or $C_2$-$C_{20}$ alkenyl.

An active ingredient combination of at least two of the abovementioned compounds is preferably obtained, such as, for example, 2, 3, 4, 5, 6, 7 or 8 individual compounds, with the group of resveratrol precursors (especially deoxyrhaponticin and deoxyrhapontigenin) and of piceatannol precursors (especially rhaponticin and rhapontigenin) each being represented by one compound.

A further preferred embodiment of the process of the invention provides an extract which has a high content of glycosides, in particular glycosides of the type described above, such as, for example, a content of from 30 to 100% by weight, 50 to 100% by weight, 60 to 99% by weight or 80 to 98% by weight or 85 to 96% by weight, in each case based on the total weight of the resulting dry extract.

A "dry extract" in the sense of the invention is present in particular when the residual moisture content of water and/or organic liquid (such as extractant) is less than about 5% by weight, in particular less than 2% by weight, such as, for example, 0 to 1.5% by weight or 0.1 to 0.5% by weight, in each case based on the total weight of the resulting dry extract.

A further preferred embodiment provides an extract which is substantially free of aglycone derivatives of rhaponticin and deoxyrhaponticin, such as, in particular, resveratrol and piceatannol. "Substantially free" means an aglycone content of less than 5% by weight, in particular less than 2% by weight such as, for example, less than 1% by weight or 0.1% by weight, such as 0 to 0.05% by weight, in each case based on the total weight of rhaponticin and deoxyrhaponticin.

Active ingredient combinations which are further preferably prepared are those having a total hydroxystilbene content, in particular a total content of deoxyrhaponticin, deoxyrhapontigenin, rhaponticin and rhapontigenin, or a total content of rhaponticin and deoxyrhaponticin, of more than 90% by weight such as, for example, 91 to 100% by weight, or 92 to 99 or 93 to 98 or 94 to 97% by weight.

Further active ingredient combinations which are preferably prepared are those having a content of less than 0.5% by weight, such as, for example, 0-0.49% by weight or 0.001 to 0.3 or 0.01 to 0.2 or 0.01 to 0.1% by weight, of anthraquinone and/or anthraquinoids (in each case based on the dry weight of the active ingredient combination). Anthraquinoids are in this case to be understood in the widest sense as substances having a basic anthraquinone structure.

In a preferred embodiment, the medicinal plant is selected from natural plants and plants modified by breeding or recombinant, genetically modified plants which have a content of at least one of the desired ingredients which is higher by comparison with the corresponding unmodified plant. These plants are selected in particular from plants of the genus *Rheum* spp., *Astragalus* spp., *Cassia* spp. or *Picea* spp. or active ingredient-containing plant parts. Nonlimiting examples of suitable species of these genera are *Rheum undulatum, Rheum palmatum, Rheum tataricum, Rheum officinale, Rheum wittrockii, Rheum altaicum, Rheum reticulatum, Astragalus complanatus, Cassia garrettiana* and *Picea sitchensis*. It is additionally preferred to employ medicinal plants as single varieties.

The skilled worker is additionally aware that genera/species differing in provenance and differing in age (i.e. harvest at various times of the vegetation period) can be employed, in turn possibly influencing the nature, amount and composition of the hydroxystilbenes and mixtures which can be isolated therefrom. It is likewise possible in principle to use various plant parts such as roots, rhizomes, leaves and/or stalks.

The respective plant part or mixture of plant parts can, if expedient, be mechanically treated prior to the extraction such as, for example, ground, chopped, reeled, crushed or cut. If expedient, predrying is also possible, such as, for example, 2 hours to 2 days at 30 to 50° C., in order to reduce the liquid content.

The hydroxystilbene-containing part of the medicinal plant used for the extraction is in particular the root of the medicinal plant, such as, for example, of *Rheum rhaponticum*.

The invention relates in particular to a process in which a hydroxystilbene-containing percolate is produced from the drug. A "percolation" means a continuous extraction of soluble substances from a drug by continual renewal of the solvent. This results in a permanent concentration gradient, so that a large part of all the soluble substances goes into the extract.

An alternative possibility is also a continuous or periodic mixing of the batch such as, for example, by stirring or shaking.

The temperature during the extraction according to the invention is usually in the range from 10 to 50° C., such as, for example, 25 to 35° C. The pressure is usually atmospheric pressure. If a speeding up of the rate of extraction or quality of the extract can be achieved, the pressure may also be varied during the extraction, such as, for example, raised or lowered.

The extraction may take, depending on the chosen conditions such as the nature of the drug, batch size, extractant and temperature used, from 1 hour to several days, such as, for example, 10 to 72 hours.

The extraction process can if necessary be repeated several times in order to ensure that isolation in particular of the desired ingredients is as complete as possible. The ratio by weight of introduced drug to liquid extractant may vary over a wide range and from extraction step to extraction step. The ratio by weight of drug to extractant is typically in the range from 10:1 to about 1:200 or about 1:2 to 1:50, or 1:4 to 1:10.

In one variant of the process, an extraction is carried out with an aqueous extractant which is substantially free of organic solvent, such as, in particular, water, preferably purified water, at a pH of the mixture in the alkaline range, with the pH of the mixture being in particular in the range from about 11 to 12, such as, for example, about 11.3 to 11.8.

The pH of the mixture is adjusted for example with the aid of an inorganic base selected from alkali metal and alkaline earth metal hydroxides such as, for example, calcium hydroxide or calcium oxide. It is possible for this purpose for example to prepare a concentrated quicklime solution by dissolving 3 to 8 parts of CaO in 20 parts of purified water. This solution is strongly alkaline and has a pH in the range from about 12 to 13, such as, for example, of about 12.4 to 12.6.

The ratio of the amounts of introduced drug to base such as, for example, calcium hydroxide (calculated as calcium oxide) can be according to the invention in the range from about 5:1 to 20:1, such as about 8:1 to 12:1 or 9:1 to 11:1.

The process is preferably carried out in such a way that the desired hydroxystilbenes are precipitated from the resulting alkaline liquid extract phase, for example by adjusting the pH of the extract to a value in the range from about 3 to 4, such as, for example, 3.2 to 3.8, or 3.4-3.6, and, where appropriate, subsequently removing the precipitate, washing where appropriate and drying where appropriate.

Used for the acidification is any inorganic or organic acid, such as, for example, hydrochloric acid or sulfuric acid, but in particular organic acids such as formic acid or acetic acid.

Before removal of the precipitate it may be expedient to leave the batch to stir for some hours or days in order to achieve precipitation which is as quantitative as possible of the desired extracted ingredients.

The precipitate can be washed for example with purified water, and this serves in particular to remove remaining acid.

Remaining liquid is removed from the extract by drying, e.g. at 30 to 50° C. or 35 to 45° C., for example over a period of from 1 to 100 hours, until the residual moisture is in the range indicated above. The drying takes place in a manner known per se, e.g. in a drying oven. Freeze drying is likewise possible.

In a further variant of the process, the extractant used is a polar aprotic organic solvent or aqueous or nonaqueous solvent mixtures comprising at least one of these organic solvents.

The organic solvent is preferably selected from $C_1$-$C_4$ alkanols and di-($C_1$-$C_4$) ketones and mixtures thereof, such as, in particular, methanol, ethanol, n- or i-propanol, aqueous alcohol such as in particular with a water content of from 1 to 90% by weight or 10 to 30% by weight or 5 to 14% by weight, such as aqueous ethanol, and ketones such as acetone and methyl ethyl ketone.

The organic or aqueous-organic liquid extract phase obtained in this case is in particular further purified in a manner known per se, such as, for example, by chromatography, and/or the extractant is removed, and dried as described above.

The extract produced according to the invention can be used directly, without further after-treatment, for producing the composition desired in each case. Further treatment of the constituents, such as, for example, a derivatization such as, for example, esterification, deglycosylation, conversion into a suitable salt, is possible in principle, however.

The invention further relates to the use of a hydroxystilbene-containing drug extract obtainable by a process as defined above for producing a composition such as, for example, selected from medicaments such as homeopathic remedies, other medicinal plant preparations, dietary supplements and dietetic food products.

The medicament or pharmaceutical composition may in particular include a solid dosage form.

This solid dosage form includes in particular an active ingredient-containing solid core with a pharmaceutically acceptable carrier and an active ingredient content of about 1 to 20% by weight, such as, for example, 2 to 15 or 5 to 10% by weight, based on the total weight of the core, where the "active ingredient" includes a hydroxystilbene-containing extract which has been produced in the above manner and which comprises hydroxystilbene constituents of the drug as defined above, especially piceatannol and/or resveratrol prodrugs.

The active ingredient combination in the composition of the invention includes in particular substantially rhaponticin and deoxyrhaponticin in a ratio of about 2:1 to 1:2 by weight.

Examples of active ingredient combinations obtainable according to the invention consist substantially of about 60-66% by weight rhaponticin
30-35% by weight deoxyrhaponticin
0-2% by weight rhapontigenin and
0-2% by weight deoxyrhapontigenin.

A dosage form may according to the invention have a total active ingredient content of about 2 to 20 mg, such as, for example, 3 to 15 or 4 to 10 mg, per dose unit.

A preferred solid dosage form additionally has a lactose-free core.

Solid dosage forms which are preferably produced are in the form of a pill, of a tablet, of an extrudate or of granules.

A further preferred solid dosage form additionally has a gastro-resistant coating.

The invention further relates to the use of a hydroxystilbene-containing drug extract produced by a process as defined above for producing a composition for the treatment of menopausal symptoms in women, juvenile oligomenorrhea and dysmenorrhea, primary and secondary amenorrhea or endometritis, of prostate cancer and disorders of the lower urogenital tract, of cancer, of chronic inflammatory disorders, of depressions and anxiety, of osteoporosis, and of headaches and migraine, especially for the treatment of menopausal symptoms in the peri- or postmenopause, such as, in particular, of hot flushes, sweating episodes, sleep disorders, irritability, psychological and mental exhaustion, sexual problems and urinary tract symptoms. The compositions produced according to the invention are particularly suitable for the treatment of menopausal symptoms owing to a natural or therapeutically induced menopause.

Owing to the excellent tolerability of the active ingredients or active ingredient combinations described above, the invention also relates to the use during long-term therapy, which is possible without limitation in time. The daily dose to be administered in this connection can be in the range from 0.1 to 20 mg or 0.5 to 15 mg, 1 to 10 or 4 to 8 mg of active ingredient or active ingredient combination such as, for example, ERr 731®.

The invention relates in particular also to a process for producing the compositions defined above, where initially an extraction process as defined above is carried out, and the hydroxystilbene-containing drug extract resulting therefrom is formulated in a manner known per se together with conventional ancillary substances to one of the abovementioned compositions.

2. Further Specific Refinements of Formulations Produced According to the Invention 2.1 Medicaments The invention also includes the production of pharmaceutical compositions (medicaments), such as homeopathic remedies, for the treatment of an individual, preferably a mammal, in particular a human, productive or domestic animal. Thus, the active ingredients or active ingredient combinations described above are usually administered in the form of pharmaceutical compositions which comprise a pharmaceutically acceptable excipient with at least one active ingredient of the invention, in particular a mixture of a plurality of active ingredients of the invention, and, where appropriate, further active ingredients. These compositions can be administered for example by the oral, local, rectal, transdermal, subcutaneous, intravenous, intramuscular, intraperitoneal, intracutaneous or intranasal route.

Examples of suitable pharmaceutical formulations are solid pharmaceutical forms such as oral powders, dusting powders, granules, tablets, such as coated tablets, gastro-resistant coated tablets, dry-coated, inlay and layered tablets, pastilles, chewable tablets, suckable tablets, sachets, cachets, sugar-coated tablets, capsules such as hard and soft gelatin capsules, pessaries, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops, nose drops, nasal spray and tinctures. It is also possible to use implanted delivery devices for administering inhibitors of the invention. Liposomes, microspheres or polymer matrices can also be used in addition.

In the production of the compositions, active ingredients or active ingredient combinations of the invention are usually mixed with an excipient or diluted. Excipients may be solid, semisolid or liquid materials which serve as vehicle, carrier, adsorbent or medium for the active ingredient or the active ingredient combinations.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, cellulose derivatives such as, for example, methylcellulose, water, syrups and methylcellulose. The formulations may in addition comprise pharmaceutically acceptable carriers or usual ancillary substances such as lubricants, for example tallow, magnesium stearate and mineral oil; wetting agents; emulsifying and suspending agents; preservatives such as methyl and propyl hydroxybenzoates; antioxidants; antiirritants; chelating agents; tablet-coating aids; emulsion stabilizers; film formers; gel formers; odor-masking agents; taste correctives; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients such as binders, fillers, lubricants, disintegrants or coatings; propellants; dessicants; opacifiers; thickeners; waxes; plasticizers; white oils.

An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996; cf. also Hager's Handbuch der Pharmazeutischen Praxis, Springer Verlag, Heidelberg.

In a preferred embodiment, a pharmaceutical composition which comprises a solid dosage form is provided. This solid dosage form in turn includes an active ingredient-containing solid core with a pharmaceutically acceptable carrier and an active ingredient content of about 1 to 20% by weight, based on the total weight of the core, where the active ingredient or the active ingredient combination includes a compound selected from resveratrol and piceatannol prodrugs; and resveratrol and piceatannol; and the stereoisomeric forms thereof, in each case in the form of their salts or in the phenol form, or combinations of at least two of these compounds. Preferred active ingredient combinations are as defined above.

This solid dosage form has for example a total active ingredient content of about 1 to 20 mg, such as, for example, 2 to 10 mg, per dose unit and can be in the form of a pill, a tablet, an extrudate or granules, and for example be sugar-coated. If desired, it may also have a gastro-resistant coating.

The solid dosage form is produced for example by mixing the active ingredient or the active ingredient combination with the pharmaceutically acceptable carrier, and consolidating the mixture to give the active ingredient core. This entails dissolving or dispersing the active ingredient or the active ingredient combination in an inert liquid, mixing it with the carrier and removing the solvent during or after the consolidation. The active ingredient core can then be provided where appropriate with a gastro-resistant coating before the core is sugar-coated in a conventional way. Such coatings are for example free of plasticizers such as phthalates, such as, for example, diethyl phthalate. Coating compositions suitable in particular for producing gastro-resistant, plasticizer-free coatings are selected from known natural and synthetic coating compositions (cf., for example, Voigt, Pharmazeutische Technologie, 7th edition 1993, Ullstein Mosby, Berlin). Particularly suitable coating compositions are, without being restricted thereto, shellac and cellulose derivatives such as hydroxypropylmethylcellulose derivatives such as, for example, hydroxypropylmethylcellulose acetate succinate, obtainable under the proprietary name AQOAT.

Mention should be made in particular of a solid dosage form with a total weight in the range of about 150 mg ±20 mg, a core weight of 84 mg ±10 mg and an active ingredient content of about 3 to 10 mg.

Further suitable solid dosage forms are those having a uniformity of active ingredient content (averaged over 10 or 20 randomly selected individual dose units) not exceeding ±5% by weight, such as, for example, ±0.1 to 4 or ±0.5 to 3 or ±1 to 2% by weight, based on the active ingredient content in the dosage form (e.g. determined as specified in Ph. Eur. 5th edition 2005 (5.0/2.09.06.00)).

Liquid dosage forms of the invention are produced for example by dissolving the active ingredient(s) such as, for example, an ERr731® dry extract in a suitable solvent such as, for example, a water/alcohol mixture, where appropriate together with further conventional additions. Active ingredient contents of from 0.1 to 20 or 1 to 10 mg/ml are usually adjusted in this case.

Semisolid dosage forms of the invention, such as, for example, gels, are produced for example by dissolving the active ingredient(s), such as, for example, an ERr 731® dry extract, in a suitable solvent such as, for example, a water/alcohol mixture, alcohol or glycerol, and incorporating the solution into the previously swollen gel former, where appropriate together with further conventional additions. Active ingredient contents of from 1 to 12 or 2 to 6 mg per gram of the formulation are usually adjusted in this case.

Solvents which should be particularly mentioned as suitable according to the invention for producing formulations are monohydric or polyhydric alcohols such as, in particular, ethanol, glycerol and mixtures thereof with water, such as, for example, 10 to 50% by volume ethanol in water.

Dosage forms or pharmaceutical compositions of the invention are produced by using generally known methods of pharmaceutical technology as described for example in Voigt, Pharmazeutische Technologie, 7th edition 1993, Ullstein Mosby, Berlin.

The mode and duration of administration of the medicaments of the invention are subject to the decision of the treating physician. The latter can establish a suitable dose and an appropriate dosage regimen depending on the chosen route of administration, on the efficacy of the specific active ingredient composition, the nature and severity of the disorder to be treated, the patient's condition and his response to the therapy. For example, a suitable single dose may comprise about 0.1 to 50 mg, such as, for example, 2 to 12 or 2 to 20 mg, of active ingredient or active ingredient combination as defined above, and be administered 1 to 3 times a day until the desired result of the treatment is to be observed.

2.2 Dietary Supplements and Food Products

The compositions of the invention also include in particular dietary supplements and food products, especially functional or dietetic food products. The food products of the invention have besides a function mainly related to nutritional value in addition a function related to active ingredients relating in particular to the active ingredient combination of the invention. They are therefore referred to as functional or dietetic food products or foodstuffs. Dietary supplements serve to supplement the daily diet with the active ingredient combination of the invention, in which case the function related to nutritional value of the dietary supplement becomes of less intrinsic importance.

The formulation base for dietary supplements and food products of the invention likewise includes physiologically acceptable ancillary substances in the widest sense, such as, for example, the abovementioned excipients. Ancillary substances in the sense according to the invention may also have a nutritional value and therefore generally be used as dietary component. Nutrients, especially essential nutrients, may also belong thereto.

Nutritional components ordinarily comprise one or more amino acids, carbohydrates or fats and are suitable for human and/or animal nutrition. They include single components, frequently vegetable, but also animal, products, especially sugars, where appropriate in the form of syrups, fruit preparations such as fruit juices, nectar, fruit pulps, purees or dried fruits, for example apple juice, grapefruit juice, orange juice, apple puree, tomato sauce, tomato juice, tomato puree; cereals products such as wheat flour, rye flour, oat flour, cornflour, barley flour, spelt flour, corn syrup, and starches from said cereals; dairy products such as milk protein, whey, yogurt, lecithin and lactose.

Examples of essential nutrients are in particular vitamins, provitamins, minerals, trace elements, amino acids and fatty acids. Essential amino acids which may be mentioned are isoleucine, leucine, lysine, methionine, phenylalanine, threonine, tryptophan and valine. These also include semiessential amino acids which must be supplied for example during growth phases or deficiency states, such as arginine, histidine, cysteine and tyrosine. Trace elements which may be mentioned are: essential trace elements and minerals such as: iron, copper, zinc, chromium, selenium, calcium, magnesium, sodium, potassium, manganese, cobalt, molybdenum, iodine, silicon, fluorine, chlorine, phosphorus, tin, nickel, vanadium, arsenic, lithium, lead, boron. Fatty acids which may be mentioned as essential for humans are: linoleic acid and linolenic acid, ARA (arachidonic acid) and DHA (docosahexaenoic acid) for infants and possibly EPA (eicosapentaenoic acid) and DHA also for adults. A comprehensive list of vitamins is to be found in "Referenzwerte für die Nährstoffzufuhr", 1 st Edition, Umschau Braus Verlag, Frankfurt am Main, 2000, edited by the Deutsche Gesellschaft für Ernährung.

Examples of suitable formulations for dietary supplementation are capsules, tablets, pills, powder sachets, liquid ampoules and bottles with dropper inserts, and the pharmaceutical forms mentioned above.

Food product formulations ordinarily have the usual form and are made available for example as breakfast preparations, in the form of mueslis or bars, sports drinks, complete meals, dietetic preparations such as diet drinks, diet meals and diet bars.

Dietary supplements and food products of the invention are produced by methods familiar to the skilled worker and requiring no further explanation (cf. for example, Hans-Dieter Belitz et al. Lehrbuch der Lebensmittelchemie. Springer-Lehrbuch 5th revised edition 2001. XLIV, 1059 publisher: SPRINGER, BERLIN)

The content of active ingredients/active ingredient combinations of the invention in the above dietary supplements and food products can vary over a wide range and is for example in a range from 0.01 to 10% by weight, such as, for example, 0.1 to 1% by weight.

The invention is now explained in more detail by means of the following nonlimiting production and formulation examples.

EXPERIMENTAL SECTION

General Methods:
Determination of Stilbenes by High-Pressure Liquid Chromatography (HPLC) in the Dry Extract from Rhapontic Rhubarb Root
a) Sample Preparation:

50 mg of extract, mixed with 40 ml of a mixture of acetone and water (1:1) in an amber glass vessel, treated in an ultrasonic bath for 15 minutes and made up to 50 ml with the solvent mixture and then diluted 1:10 with the solvent mixture.
b) Procedure for the Chromatography:

A high-pressure liquid chromatography (HPLC) is carried out on a portion of the solution obtained above, with the following system parameters:

| | |
|---|---|
| Sample loop: | 20 µl |
| Column: | Lichrospher 5µ RP 18, 250 × 4 mm |
| Precolumn: | Lichrospher 5µ RP 18, 5 × 4 mm |
| Column temperature: | 25° C. |
| Eluent A: | Acetonitrile/dist. water/phosphoric acid 85%, 15/85/0.05 (parts by volume) |
| Eluent B: | Acetonitrile/dist. water/phosphoric acid 85%, 80/20/0.05 (parts by volume) |
| Flow rate: | 1.5 ml/min |
| Column flushing: | 15 min with eluent 50% B; equilibration time 15 min |
| Detection: | 310 nm |
| HPLC: | Kontron Kroma 2000 |
| | Time    % B |
| Gradient: | 0.0    0 |
| | 0.5    0 |
| | 7.5    75 |
| | 8.5    100 |
| | 9.5    0 |
| | 12.5    0 |

The retention times resulting under the system conditions indicated above are as follows:

| | |
|---|---|
| Rhaponticin: | about 5.5 min |
| Deoxyrhaponticin: | about 6.8 min |
| Rhapontigenin: | about 7.2 min |
| Deoxyrhapontigenin: | about 9.0 min |

For a quantitative determination, the respective peak areas are found and compared with the corresponding peak areas of a standard extract of known composition.

PREPARATION EXAMPLE 1

Preparation of the Dry Extract ERr 731 from Rhapontic Rhubarb Root with an Aqueous Calcium Hydroxide Solution A dry extract is prepared from rhapontic rhubarb root employing the following:

| | |
|---|---|
| Drug (radix rheum rhaponticum) | 50.0 kg |
| Calcium oxide | 5.0 kg |
| Purified water | 190.0 kg |

Acetic acid (as necessary to adjust the required pH)

The yield which can be achieved in this case is between 2 and 3 kg per 50 kg of drug.

The preparation takes place in the following steps:
a) Firstly 5 kg of calcium oxide are introduced into a plastic tub and made into a slurry with 20 kg of purified water. The formation of calcium hydroxide (quicklime) which takes place under these conditions leads to a large rise in temperature of the solution. The calcium hydroxide can therefore be used further only after cooling. The temperature of the solution is then 30° C. to 35° C.
b) 50 kg of drug are introduced into a mixer, and the above-mentioned quicklime is added. In order to remove the quicklime as completely as possible from the plastic tub, it is rinsed with 10 kg of purified water. This washing liquid is likewise put in the mixer.
c) The drug homogeneously mixed with quicklime is introduced into a percolator and covered with 160 kg of purified water. The percolator remains closed for 48 hours. The percolate is then collected in a suitable vessel at a flow rate of 50 ml/min. The percolation is continued until no further percolate emerges. The drug mass is not squeezed out after completion, but is discarded.
d) While monitoring continuously, concentrated acetic acid is added to the percolate until a pH in the range from 3.4 to 3.6 is reached. In order to achieve precipitation of the extract which is as complete as possible, the mixture is left to stand for 5 days.
e) The dry extract is obtained by filtration through Büchner funnels under applied vacuum. Finally, the extract is washed with 10 to 20 kg of purified water.
f) The dry extract obtained after filtration is dried in a drying oven at 40° C. until a residual moisture tolerance not exceeding 1% is reached.

Rhaponticin is readily soluble in aqueous solutions with an alkaline pH range, whereas it is precipitated as yellowish substance in the acidic pH range (pH 3.4-3.6). Use is made of this for its isolation. Since, besides other organic acids, the root in particular has a high content of oxalic acid (⅔ in water-soluble and ⅓ in bound form), this must be neutralized during the isolation in order to prevent the pH drifting into the acidic range and thus to inhibit premature precipitation of the rhaponticin. This is achieved by using calcium oxide. The latter is employed as quicklime solution with a pH of 12.4-12.6.

Homogeneous mixing of the quicklime with the drug alters the pH of the mixture. It is then in the range from 11.3 to 11.8, thus preventing precipitation of rhaponticin, because the phenolic form has been converted into a phenolate form. Despite the high oxalic acid content, the pH can be kept in the alkaline range. This is attributable to the fact that the calcium hydroxide reacts with oxalic acid and forms insoluble and nontoxic calcium oxalate.

Rhaponticin is extracted from the root by the subsequent percolation with purified water. After completion of the percolation, a pH of 3.4 to 3.6 is adjusted by adding acetic acid. This pH shift from the alkaline to the acidic range leads to a precipitation of rhaponticin through conversion back into the phenolic form. In order to achieve precipitation of rhaponticin which is as complete as possible, the mixture is left to stand for 5 days. It is then filtered. Rhaponticin remains as yellowish substance on the filter.

The above statements about rhaponticin apply correspondingly to the other hydroxystilbene active ingredients isolated according to the invention.

PREPARATION EXAMPLE 2

Preparation of a Dry Extract from Rhapontic Rhubarb Root with Various Organic Solvents The constituents mainly detectable in the rhapontic rhubarb root used as drug here belong to the group of hydroxystilbenes. Present from this group in the roots are rhaponticin (Rh) with a content of about 6% and deoxyrhaponticin (DRh) with a content of about 4%.

It is possible by exposure to the solvent systems indicated below, in a 100-fold quantity at room temperature for 10 minutes with shaking or stirring, to extract the proportions summarized below:

| | | |
|---|---|---|
| Ethanol 86% | Rh | 100.8% |
| | DRh | 99.5% |
| Ethanol 15% | Rh | 77.1% |
| | DRh | 75.5% |
| Acetone | Rh | 88.3% |
| | DRh | 96.6% |
| Water, alkaline (pH 11, adjusted with CaO solution) | Rh | 75.5% |
| | DRh | 60.5% |

No useful results were achieved with heptane.

The respective yields of crude extracts in proportions by mass (based on drug employed) are as follows:

| | |
|---|---|
| Ethanol 86% | 35.5% |
| Ethanol 15% | 32.2% |
| Acetone | 21.4% |
| Heptane | 0% |
| Water, alkaline | 4.5% |

Extraction of rhapontic rhubarb root with ethanol-water mixtures leads to an extract which, besides the main constituents rhaponticin (about 30%) and deoxyrhaponticin (about 22%), comprises a further stilbene, which has not as yet been investigated, in a proportion of about 20% in the extract. Besides these, the aglycones rhapontigenin (about 8%) and deoxyrhapontigenin (about 2%) and a further 9 compounds which total about 20% are obtained.

The results on extraction with acetone are fundamentally the same.

Extraction with alkaline water (cf. conditions in preparation example 1) leads to an extract of greater purity.

The main constituents rhaponticin and deoxyrhaponticin are present in a proportion of about 97% in the dry extract. Rhapontigenin and deoxyrhapontigenin together amount to a proportion of 1.1% of the extract, whereas the stilbene which has not yet been investigated is present in a proportion of only 0.2%. A further 3 compounds are present in a proportion of 2.5%.

FORMULATION EXAMPLE 1

Production of a Solid Dosage Form—Minitablet

1. Production of the Tablet Core:

A solid tablet core is produced using the following active ingredients and ancillary substances in the stated ratios of amounts (P=parts by weight). The ingredients are mixed and tabletted in three different ways:

a) Tablet Core Formulation:

| | |
|---|---|
| Purified dry extract according to preparation example 1 from rhapontic rhubarb root (ERr 731 ®) | 3.6 P |
| Microcrystalline cellulose (e.g. Avicel ®) | 57.0 P (±40%) |
| Sorbitol | 8.0 P (±40%) |
| Talc | 2.5 P (±40%) |
| Makrogol 6000 (polyglycol) | 1.6 P (±40%) |
| Polyvidone (K value about 25, e.g. Kollidon ® 25) | 1.6 P (±40%) |
| Sodium dodecyl sulfate (e.g. Texapon ® K 12) | 0.5 P (±40%) |
| Magnesium stearate (vegetable) | 0.8 P (±40%) |
| | 75.6 P (±40%) |

It is possible by varying the weighed amount of ERr 731® and/or varying the amount of microcrystalline cellulose to obtain any desired ERr 731® contents in the untreated core (such as, for example, 2, 4, 6, 8, 10, 12 mg per tablet).

b) Mixing of Drug and Carrier

Mixing Variant a:

1.2 P of ERr 731® are triturated in portions with Avicel® in a ball mill and then, after addition of the other ancillary substances, mixed and tabletted as described below.

Mixing Variant b:

ERr 731® (1 g/l of solvent) is dissolved in a suitable solvent (e.g. ethanol/water mixture 86% v/v ethanol) and adsorbed on Avicel®, dried (at 40° C. for at least 48 hours) and, after addition of the other ancillary substances, mixed and tabletted as described below.

Mixing Variant c:

The total amount of Avicel® is divided into three equal portions. The first portion is mixed with the total amount of ERr731® and triturated in a laboratory ball mill (e.g. type 1-25 LK, Alpine, Augsburg) for at least 120 minutes. The second portion of Avicel® is then added, and the mixture is again triturated in the laboratory ball mill for at least 120 minutes. After addition of the third portion of Avicel®, brief mixing is again carried out. Subsequently, after addition of the other ancillary substances, mixing and tabletting are carried out as described below.

It is surprisingly possible with this mixing variant to reduce markedly the tendency to inhomogeneity and, even with small dose units, to adjust an extremely uniform active ingredient content of not more than ±5% by weight (determined according to Ph. Eur. 5th edition 2005 (5.0/2.09.06.00)).

c) Tabletting:

The mixture of Avicel® and active ingredient is sieved through a sieving machine (sieve diameter 1.2 mm) into a suitable mixing container and, after addition of the stated tabletting aids (without magnesium stearate), mixed in a suitable mixer (e.g. drum hoop mixer of type Standard RR M 200, from Engelsmann AG/Ludwigshafen) for at least 30 min. Addition of magnesium stearate is followed by mixing again for at least 5 min.

The compression takes place in a suitable tablet press (e.g. rotary of type Perfecta Fette 2000, from Fette/Schwarzenbeck):

| Core weight: | 84 mg ± 4.2 mg maximum variation |
|---|---|
| Punch: | 7 mm diameter, domed |

The ERr-731 content per core is about 4 mg ±5%.

2. Production of the Gastro-Resistant Coated Tablet

After removal of dust from the tablet cores with Eudragit, a gastro-resistant coating of cellulose acetate phthalate and diethyl phthalate, dissolved in isopropanol and ethyl acetate, is applied to the tablet cores using a coating system.

Macrogol is dissolved in purified water. The ingredients sugar (sucrose or isomalt), calcium carbonate, talc, titanium dioxide and the two povidones are mixed and stirred into the liquid. The suspension is stirred in a jet flow mixer (e.g. Rototron of type RTA 70-50) for 20 minutes.

The sugar-coating suspension is applied to the sealed core with the aid of an automatic coater. The process is repeated until an average weight of 150 mg per coated core is reached. Finally, the polishing wax is applied and then rolling is continued until a high gloss is obtained.

Final Weight of the Gastro-Resistant Coated Tablet: 150 mg ±7.5 mg maximum variation.

In this way, two different tablet forms—one containing sugar and one sugar-free—are produced, employing the respective ancillary substances in the parts by weight indicated below.

a) Gastro-Resistant Coated Minitablet—Containing Sugar—with Plasticizer in the Coating

| Ancillary substances: | | |
|---|---|---|
| Coating: | Eudragit L12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |
| | Talc | 2.000 kg (±40%) |
| Sugar coating: | Talc | 7.182 kg (±40%) |
| | Sugar | 28.747 kg (±40%) |
| | Calcium carbonate | 6.410 kg (±40%) |
| | Titanium dioxide E 171 | 0.635 kg (±40%) |
| | Povidone (K value about 25, e.g. Kollidon ® 25) | 0.756 kg (±40%) |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) | b) Gastro-Resistant Coated Minitablet—Sugar-Free—with Plasticizer in the Coating

| Ancillary substances: | | |
|---|---|---|
| Coating: | Eudragit L12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |

| Ancillary substances: | | |
|---|---|---|
| Sugar coating: | Talc | 7.482 kg (±40%) |
| | Sorbitol and/or isomalt | 28.747 kg (±40%) |
| | Calcium carbonate | 6.410 kg (±40%) |
| | Titanium dioxide E 171 | 0.635 kg (±40%) |
| | Povidone (K value about 25, e.g. Kollidon ® 25) | 0.756 kg (±40%) |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) |

FORMULATION EXAMPLE 2

Production of a Solid Dosage Form—Minitablet Containing Sugar Without Plasticizer 1. Production of the Tablet Core
Production takes place in analogy to formulation example 1.

2. Production of the Gastro-Resistant Coated Tablet
Production takes place in analogy to formulation example 1, but with use of shellac (variant A) or Aqoat (variant B) instead of cellulose acetate phthalate/diethyl phthalate (plasticizer).

a) Variant A

| Ancillary substances: | | kg (±40%) |
|---|---|---|
| Coating: | Eudragit L12.5% dry matter | 0.400 |
| | CAPOL 5270 PH 8% (shellac solution) = 4.8 kg dry matter (shellac) | 60.000 |
| | Isopropyl alcohol | 4.000 |
| | Ethanol 96% | 3.200 |
| | Talc | ..2.000 |
| Sugar coating: | Talc | 7.182 |
| | Sugar | 28.747 |
| | Calcium carbonate | 6.410 |
| | Titanium dioxide E 171 | 0.635 |
| | Polyvidone (K value about 25, e.g. Kollidon ® 25) | 0.756 |
| | Povidone (K value: about 90) | 0.332 |
| | Macrogol 35,000 | 0.635 |
| | Water | 10.500 |
| Polish: | 95% carnauba wax 5% bleached wax (e.g. Capol 1295 PH) | 0.108 | b) Variant B

| Ancillary substances: | | kg (±40%) |
|---|---|---|
| Coating: | Eudragit L12.5% dry matter | 0.400 |
| | Aqoat Hydroxypropylmethylcellulose acetate succinate | 5.420 |
| | Distilled water | 12.500 |
| | Isopropyl alcohol | 4.000 |
| | Ethanol 86% | 55.000 |
| Sugar coating: | Talc | 9.182 |
| | Sugar | 28.747 |
| | Calcium carbonate | 6.410 |
| | Titanium oxide E 171 | 0.635 |

-continued b) Variant B

| Ancillary substances: | | kg (±40%) |
|---|---|---|
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

FORMULATION EXAMPLE 3

Production of a Solid Dosage Form—Minitablet Sugar-Free Without Plasticizer

1. Production of the Tablet Core

Production takes place in analogy to formulation example 1, but using isomalt instead of Avicel.

2. Production of the Gastro-Resistant Coated Tablet

Production takes place in analogy to formulation example 2, but using isomalt instead of sugar.

a) Variant A

| Ancillary substances: | | kg (±40%) |
|---|---|---|
| Coating: | Eudragit L12.5% dry matter | 0.400 |
| | CAPOL 5270 PH 8% | 60.000 |
| | (shellac solution) = | |
| | 4.8 kg dry matter (shellac) | |
| | Isopropyl alcohol | 4.000 |
| | Ethanol 96% | 3.200 |
| | Talc | 2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | | b) Variant B

| Ancillary substances: | | kg (±40%) |
|---|---|---|
| Coating: | Eudragit L12.5% dry matter | 0.400 |
| | Aqoat | 5.420 |
| | Distilled water | 12.500 |
| | Isopropyl alcohol | 4.000 |
| | Ethanol 86% | 55.000 |
| | Talc | ..2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. | |
| | Kollidon ® 25) | |

-continued b) Variant B

| Ancillary substances: | | kg (±40%) |
|---|---|---|
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

FORMULATION EXAMPLE 4

Production of a Semisolid Dosage Form—Vaginal Gel

Production takes place using conventional methods by the two following variants:

a) Variant A:

Hydroxypropylmethylcellulose (hypromellose USP) or another gel former is allowed to swell with 2-10% by weight in purified water. The ERr 731® (preparation example 1), dissolved in glycerol, is then incorporated. The amount of glycerol may be up to 50% of the weight of the gel. ERr 731® can be dissolved up to 0.5% by weight in glycerol. If necessary, preservatives (e.g. sorbic acid and its salts) can be added to the gel. Adjustment of the pH is also possible. As alternative to glycerol it is also possible to use 30-86% by volume ethanol.

b) Variant B:

Carbomer (Carbopol) is dissolved with 0.5-5% by weight in purified water, and the desired pH is adjusted (e.g. KOH, NaOH, $NH_3$). If necessary, a preservative (e.g. sorbic acid and its salts) is admixed. After formation of a clear gel, ERr 731® (preparation example 1) is dissolved up to 0.5% by weight in 30-86% by volume ethanol and added. As alternative to ethanol, it is also possible to use glycerol.

FORMULATION EXAMPLE 5

Production of a Semisolid Dosage Form—Vaginal Suppositories

Suppositories with a size of 1 to 15 g with a content of 1 to 12 mg of ERr 731® (preparation example 1) dissolved in glycerol (85% n 20/D=1.45085) are produced in a conventional way by two different variants.

| a) Variant A: Formulation: | |
|---|---|
| Gelatin | 1 part |
| Purified water | 2 parts |
| Glycerol 85% (+ERr 731 ®) | 5 parts | b) Variant B:

Same formulation but with suitable preservatives such as, for example, sorbate, benzoate, PHB ester.

The gelatin is introduced in each case into purified water and allowed to swell until the mixture has become glassy. Glycerol 85% with active ingredient is then added and heated, but not above 65° C. The suppositories are then cast in a conventional way.

FORMULATION EXAMPLE 6

Production of a Liquid Dosage Form—Drops a) Dissolving Tests with ERr 731® in Ethanol and Glycerol:
Content of the extract:
61.9% rhaponticin
29.9% deoxyrphaponticin

| Test A: 200 mg of dry extract in 50 ml of glycerol R: | |
| --- | --- |
| 55.1% rhaponticin | (89.0% of theory) |
| 27.1% deoxyrhaponticin | (90.6% of theory) |
| Test B: 200 mg of dry extract in 50 ml of ethanol 30% R: | |
| 52.2% rhaponticin | (84.3% of theory) |
| 25.2% deoxyrhaponticin | (84.2% of theory) |
| Test C: 200 mg of dry extract in 50 ml of ethanol 50% R: | |
| 58.8% rhaponticin | (95.0% of theory) |
| 29.0% deoxyrhaponticin | (97.0% of theory) |
| Test D: 200 mg of dry extract in 50 ml of ethanol 86% R: | |
| 59.8% rhaponticin | (96.6% of theory) |
| 29.5% deoxyrhaponticin | (98.7% of theory) | b) Production of Drops:

Drops are produced by dissolving dry extract according to test B in ethanol 30% R and filtering where appropriate.

The invention claimed is:

1. A process for producing a hydroxystilbene-containing drug extract, comprising:
   a) providing a hydroxystilbene-containing part of a plant of the genus *Rheum* sp.,
   b) adding an aqueous extractant to the hydroxystilbene-containing part of the plant to form a mixture, wherein said aqueous extractant is substantially free of organic solvents,
   c) extracting in a single step the mixture at a pH in the alkaline range and at a temperature range between 10 to 35° C. at atmospheric pressure, thereby obtaining a liquid extract phase from the mixture, and
   d) obtaining a hydroxystilbene-containing drug extract through precipitation, wherein said precipitation is performed by adjusting the pH of the liquid extract phase to a value between 3 to 4,
thereby producing a hydroxystilbene-containing drug extract having a total content of rhaponticin and deoxyrhaponticin of more than 90% by weight and having 0 to 0.05% by weight of piceatannol and 0 to 0.3% by weight of anthraquinoids.

2. The process as claimed in claim 1, wherein the resulting extract further includes at least one compound selected from the group consisting of rhapontigenin, deoxyrhapontigenin and the stereoisomeric forms thereof, in each case as a salt or in phenolic form.

3. The process as claimed in claim 1, wherein the hydroxystilbene-containing part of the plant is the root of *Rheum rhaponticum*.

4. The process as claimed in claim 1, wherein the mixture is extracted via percolation.

5. The process as claimed in claim 1, wherein the pH of the mixture in step c) is in the range from about 11.3 to 11.8.

6. The process as claimed in claim 1, wherein in step c), the pH of the mixture is adjusted in the alkaline range with the aid of an inorganic base selected from the group consisting of alkali metal and alkaline earth metal hydroxides.

7. The process as claimed in claim 6, wherein the base is calcium hydroxide.

8. The process as claimed in claim 7, wherein the ratio of the amount of the hydroxystilbene-containing part of the plant to calcium hydroxide, calculated as calcium oxide, is in the range from about 5:1 to 20:1.

9. The process as claimed in claim 1, wherein the precipitate is removed, washed and dried.

10. The process as claimed in claim 1, wherein the precipitate is derivatized into an ester or an ether after further purification.

11. The process as claimed in claim 10, wherein the derivatization is esterification.

12. The process as claimed in claim 10, wherein the derivatization is etherification.

13. A process for producing a composition selected from the group consisting of, medicinal plant preparations, dietary supplements and dietetic food products, comprising:
   a) producing a hydroxystilbene-containing drug extract according to a process as claimed in claim 1; and
   b) formulating the extract to give the composition.

14. The process as claimed in claim 13, wherein the medicament includes a solid, semisolid or liquid dosage form.

15. The process as claimed in claim 14, wherein the solid dosage form comprises a solid core containing the hydroxylstilbene-containing drug extract as active ingredient and a pharmaceutically acceptable carrier, wherein the content of the active ingredient is about 1 to 20% by weight based on the total weight of the core, wherein the active ingredient optionally further includes at least one compound selected from the group consisting of rhapontigenin, deoxyrhapontigenin, and the stereoisomeric forms thereof, in each case as a salt or in phenolic form, and optionally at least one compound selected from the group consisting of resveratrol, piceatannol, astringin, and the stereoisomeric forms thereof, in each case as salt or in phenolic form.

16. The process as claimed in claim 15, wherein rhaponticin and deoxyrhaponticin are present in the active ingredient in a ratio of about 2:1 to 1:2 by weight.

17. The process as claimed in claim 15, wherein the solid dosage form comprises about
   60-66% by weight rhaponticin;
   30-35% by weight deoxyrhaponticin;
   0-2% by weight rhapontigenin; and
   0-2% by weight deoxyrhapontigenin.

18. The process as claimed in claim 14, wherein the dosage form has a total active ingredient content of about 2 to 20 mg per dose unit.

19. The process as claimed in claim 14, wherein the solid dosage form has a lactose-free core.

20. The process as claimed in claim 14, wherein the solid dosage form is in the form of a pill, a tablet, an extrudate or granules.

21. The process as claimed in claim 14, wherein the solid dosage form has a gastro-resistant coating.

22. The process as claimed in claim 14, wherein the medicament is selected from the group consisting of gels and solutions.

23. A process for producing a pharmaceutical composition comprising:
   a) producing a hydroxystilbene-containing drug extract having a total content of rhaponticin and deoxyrhaponticin of more than 90% by weight, by a method comprising:
      i) providing a hydroxystilbene-containinq part of a plant of the genus *Rheum* sp., ii) adding an aqueous extractant to the hydroxystilbene-containing part of the herbal drug to form a mixture, wherein said aqueous extractant is substantially free of organic solvents, iii) extracting in a single step the mixture at a pH in the alkaline range and at a temperature range between 10 to 35 °C at atmospheric pressure, thereby obtaining a liquid extract phase from the mixture, and iv) obtaining a hydroxystilbene-containing drug extract through precipitation, wherein said precipitation is performed by adjusting the pH of the liquid extract phase to a value between 3 to 4; and b) formulating the extract to give the pharmaceutical composition.

24. The process as claimed in claim 1, further comprising providing the hydroxystilbene-containing part of the plant in comminuted form.

25. The process as claimed in claim 1, wherein the extracting of the liquid extract phase is repeated several times.

26. The process as claimed in claim 23, wherein the hydroxystilbene-containing drug extract comprises 0 to 0.05% by weight of piceatannol and 0 to 0.3% by weight of anthraquinoids.

27. The process as claimed in claim 4, wherein the hydroxystilbene-containing drug extract is obtained as a percolate by washing the mixture with water.

* * * * *